US012760251B2

(12) United States Patent
Rautiainen

(10) Patent No.: US 12,760,251 B2
(45) Date of Patent: Oct. 13, 2026

(54) REACTOR FOR MANUFACTURING BIOGAS FROM ORGANIC RAW MATERIAL USING ANAEROBIC DIGESTION

(71) Applicant: Mika Rautiainen, Leppävesi (FI)

(72) Inventor: Mika Rautiainen, Leppävesi (FI)

( * ) Notice: Subject to any disclaimer, the term of this patent is extended or adjusted under 35 U.S.C. 154(b) by 573 days.

(21) Appl. No.: 18/275,066

(22) PCT Filed: Jan. 31, 2022

(86) PCT No.: PCT/FI2022/050057

§ 371 (c)(1),
(2) Date: Jul. 31, 2023

(87) PCT Pub. No.: WO2022/162279

PCT Pub. Date: Aug. 4, 2022

(65) Prior Publication Data

US 2024/0067908 A1 Feb. 29, 2024

(30) Foreign Application Priority Data

Feb. 1, 2021 (FI) ..................................... 20215103

(51) Int. Cl.
*C12M 1/107* (2006.01)
*C12M 1/12* (2006.01)
*C12M 3/00* (2006.01)

(52) U.S. Cl.
CPC ............ *C12M 21/04* (2013.01); *C12M 23/06* (2013.01); *C12M 23/44* (2013.01); *C12M 23/48* (2013.01)

(58) Field of Classification Search
None
See application file for complete search history.

(56) References Cited

U.S. PATENT DOCUMENTS

2016/0298067 A1* 10/2016 Rautiainen ............. C12M 21/16
2020/0377834 A1 12/2020 Rautiainen et al.

FOREIGN PATENT DOCUMENTS

DE 102005049476 A1 4/2006
EP 0732308 A1 9/1996

(Continued)

OTHER PUBLICATIONS

Extended European Search Report issued by the European Patent Office for Application No. 22745432.9 dated Nov. 27, 2025, 7 pages.

(Continued)

*Primary Examiner* — William H. Beisner
(74) *Attorney, Agent, or Firm* — Boone IP Law

(57) ABSTRACT

The invention relates to a reactor for manufacturing biogas from organic raw material using anaerobic digestion, the reactor including a tubular reaction chamber composed of a bottom, walls and a ceiling for processing the raw material into end products, and agitation and transfer equipment arranged in the reaction chamber. The reactor includes an external support frame structure arranged on the outer surface included in the reaction chamber for stiffening and supporting the reaction chamber externally against the forces generated by the raw material. The shell of the reactor chamber is composed of outer shell elements and inner shell elements placed apart from each other inside a space defined by the support frame structure, which together form the housing structure of the shell, and the filling space or housing between which is concreted.

19 Claims, 6 Drawing Sheets

(56) References Cited

FOREIGN PATENT DOCUMENTS

| | | | |
|---|---|---|---|
| KR | 101792118 | B1 | 10/2017 |
| WO | 9531622 | A1 | 11/1995 |
| WO | 2009002112 | A2 | 12/2008 |
| WO | 2019102074 | A1 | 5/2019 |

OTHER PUBLICATIONS

Finnish Search Report in Patent Appln. No. FI20215103, dated Jul. 8, 2021, 1 page.

* cited by examiner

REACTOR FOR MANUFACTURING BIOGAS FROM ORGANIC RAW MATERIAL USING ANAEROBIC DIGESTION

CROSS-REFERENCE TO RELATED APPLICATIONS

This application is a National Phase entry of International Application No. PCT/FI2022/050057, filed Jan. 31, 2022, which claims priority to Finland Patent Application No. 20215103, filed Feb. 1, 2021, the disclosures of which are incorporated herein by reference in their entireties.

TECHNICAL FIELD

The invention relates to a reactor for manufacturing biogas from organic raw material using anaerobic digestion, the reactor including a tubular reaction chamber composed of a bottom, walls, and a ceiling for processing the raw material into end products, and agitation and transfer equipment arranged in the reaction chamber.

BACKGROUND

Publication WO/075298 A1 represents prior art proposing a reactor for manufacturing biogas from biowaste. The reaction chamber of the reactor is a tubular structure composed of walls, a floor, and a ceiling.

In small reactors, the hydrostatic pressure remains fairly low, and the reaction chamber can be manufactured as a fairly thin steel construction with the wall thickness of 100-150 mm.

However, a problem in a construction according to the aforementioned publication is that as the reactor size increases, the height of the raw material mattress in the reaction chamber also increases and thereby, the hydrostatic pressure exerted on the walls of the reaction chamber increases. To be able to make the reaction chamber sufficiently strong to resist stresses acting on it, the thickness of the walls of the reaction chamber must be increased proportionally to the increase of the reactor height. It is not reasonable to increase the width of prior art reactors, since then the floor area they require at production plants would increase, raising the need of covered space in the production plant and thereby investment costs. In turn, increasing the thickness of reaction chamber walls raises raw material costs, complicates the handling of the reaction chamber, and causes high costs when the reaction chamber is transported as a whole from the place of manufacture to the application site.

The object of the invention is to provide a reactor for manufacturing biogas from organic raw material using anaerobic digestion that is more advantageous for its manufacturing and transport costs than prior art reactors. The characteristic features of this invention are set forth in the appended claim 1.

By a housing structure assembled from shell elements and its reinforcement by concreting is provided a structure that is structurally optimized, cost-efficient and easily transported to its installation site, the structure being concreted after installation to provide a final robust structure. The reaction chamber is constructed from shell elements manufactured separately for this purpose which form a housing structure. After the installation of the shell elements, the housing is filled with concrete, whereupon the reaction chamber resists the hydrostatic pressure exerted on it from the inside, generated by biowaste with a high liquid content during the slow anaerobic digestion reaction. As the external support frame structure is arranged on the outer surface included in the reaction chamber, this stiffens and supports the shell element structure of the reaction chamber of even a large reactor externally during installation and concreting, as well as against forces generated by the raw material when the reactor is in use. By this structure is then achieved in a novel and inventive manner the aforementioned advantages, enabling, for example, the manufacture of reaction chambers of varied sizes using shell elements as much the same size as possible and elements to be used in the support frame structure.

SUMMARY

In a reactor according to a preferred embodiment of the invention, the sandwich elements forming the reaction chamber walls supported by an external support frame structure can be manufactured quite lightweight and from steel even less than 4 mm thick. This reduces the material and transport costs of the reaction chamber of the reactor. Further, the external support frame structure can be made, for example, of tubular beams by assembling to an extremely rigid, yet fairly lightweight structure, which supports the shell elements during installation and concreting, as well as the reaction chamber from the outside during use. The installation of a reaction chamber according to the invention is initiated by assembling the external support frame to support the outermost shell elements of the housing structure. After installation of the outermost shell elements, possible remaining concrete reinforcements are installed and, after this, the inner shell elements. The external support frame structure enables in an inventive manner the use of quite lightweight shell elements and, further, with the external frame structure, a counterforce is created for the force generated by the hydrostatic pressure inside the reaction chamber. Instead of concrete or additionally, it is possible to use some other filling substance to stiffen and reinforce the shell structure.

The reactor is advantageously a plug-flow reactor. In this case, the process can be continuously operating.

Advantageously, agitation and transfer equipment is supported to the external support frame structure. With agitation and transfer equipment, raw material can be mixed to optimize the biological action, as well as moved ahead in the reaction chamber for promoting anaerobic digestion. Supporting the agitation and transfer equipment to the external support frame structure enables, in turn, the lightweight structure of the reaction chamber, as the loads of the agitation and transfer equipment are not exerted on the reaction chamber walls, but instead on the external support frame structure.

The reactor advantageously also includes heating, reject recirculation, automation and gas recovery equipment similar to that of prior art. With the heating equipment, the reaction chamber temperature is kept sufficiently high for anaerobic digestion. In turn, digestate is advantageously recirculated always to the previous agitation zone for transferring a microbial strain. An automation system is used to control the agitation and transfer equipment, heating equipment and reject recirculation equipment for maintaining anaerobic digestion in a preferably continuous process. The aforementioned components can be similar to those proposed in the prior art publication WO 2015/075298 A1.

Advantageously, at least the walls and the ceiling of the reaction chamber are composed of modularly dimensioned shell elements. In this case, a large-size reaction chamber is easy to transport from the place of manufacture to the application site as notably smaller elements. The use of elements is particularly advantageous with an external support frame structure, since the frame is used for supporting the wall elements during installation and concreting, and no additional support structures are required.

The height of the reactor may be in the range of 3-15 m, preferably 8-10 m. Hydrostatic pressure generated by liquid material in the reaction chamber produces extremely high forces as the reactor height increases when aiming for a higher capacity.

The modularly dimensioned shell elements in the reaction chamber walls can have a height ranging 0.5-3.6 m, preferably, 0.5-2.4 m. In this way, the elements are easier to handle than large elements and they can be tightly packed in conventional marine containers minimizing the empty space that remains in the marine container.

The modularly dimensioned shell elements in the reaction chamber walls can have a length of 6-13 m, preferably 10-12 m. In this way, the shell elements are easier to handle than large elements and they can be tightly packed in conventional marine containers minimizing the empty space that remains in the marine container. At the outer corners are high corner elements.

The reaction chamber advantageously includes sealed lead-throughs for agitation and transfer equipment for keeping liquid raw material or end products in the reaction volume. This enables a sufficiently high filling rate for the reaction chamber in order to achieve good efficiency.

Advantageously, the flanges of the shell elements serve along with the reinforcing steel bars as a stiffening structure.

Advantageously, the flanges of the shell elements have ready-made holes for the reinforcing steel bars.

Advantageously, each shell element includes seals for sealing the seams between the elements. In this way, the shell elements can be made tight avoiding discharge of hydrostatic pressure in the reaction chamber between the shell elements.

The thickness of the walls (shell) of the reaction chamber can be in the range of 200-500 mm, preferably 250-350 mm. The thickness of the shell elements is preferably 80-140 mm, whereupon the weight of the prefabricated shell elements of the reaction chamber remains moderate reducing transport costs and lowering material costs during the reactor manufacture. This also defines the maximum width of the filling space or housing.

Advantageously, the shell elements, at least their casing, can be made from carbon steel. The shell elements can also be made from stainless steel. Instead of steel, the shell elements can also be made, for example, of composite, plastic, or other similar material with sufficient rigidity.

Advantageously, into the filling space or housing remaining between the shell elements is poured concrete (and, if required, added reinforcements such as rebars), but on the other hand, instead of concrete, some other material with the required strength properties can be used.

Advantageously, the external support frame structure is composed of angle irons or tubular beams that are welded to each other. Angle irons or tubular beams are sufficiently rigid components to offer sufficient stiffness, yet notably light to save weight and material. Instead of steel, the external support frame structure can be made, for example, of composite or other similar material with sufficient rigidity.

Advantageously, the external support frame structure includes vertical columns arranged at a distance from each other in the lengthwise direction relative to the reactor on both sides of the reactor, transverse support structures for connecting the vertical columns in the transverse direction relative to the reactor and longitudinal support structures for connecting the vertical columns to each other in the lengthwise direction relative to the reactor on each side of the reactor. Such an external support frame structure is notably light and can thus also be transported from the place of manufacture to the application site with low transport costs.

Advantageously, each shell element includes an edged reinforcement arranged to circulate the element for reinforcing it. With reinforcements, it is possible to increase the stiffness and load bearing capacity of the shell elements.

Advantageously, the edged reinforcement (the flange) has holes for the reinforcing steel bars.

Advantageously, the external support frame structure includes plate stiffeners fastened against the outer surface of the reaction chamber. Due to the plate stiffeners, the external support frame structure stiffens the reaction chamber in such a way that it can be supported at selected points only and the external support frame structure can be quite sparse as to its vertical columns.

Plate stiffeners are advantageously fastened between edged reinforcements in each shell element. Thus, each shell element is sufficiently stiff to receive forces acting on it.

Advantageously, the plate stiffeners have holes for the reinforcing steel bars.

The external support frame structure is advantageously composed of hollow tubes fastened together. In this way, the weight of the external support frame structure remains moderate compared to a structure manufactured from solid iron, while, on the other hand, tubes provide sufficient structural rigidity for supporting the reaction chamber. Correspondingly, the external support frame structure can also be manufactured, for example, from composite or similar material.

Advantageously, the shell elements forming the reaction chamber insulation or casing, or both, are sandwich elements provided with a stiffening casing structure and insulation. These are extremely lightweight structures.

Implementation of a reaction chamber of a reactor according to the invention advantageously with shell elements enables transportation of the reactor in marine containers or containers transported by road and delivery of reactors larger than before to customers located in poorly accessible regions. In turn, an external support frame structure provides the benefit that it is not necessary to increase thickness of walls (shell) of the reaction chamber even though the size of the reactor is increased, and no additional support structures are needed during installation and concreting of the shell elements. However, this does not preclude that, if required, the width of the filling space or housing (i.e. the width of the concreting) can be defined at the installation site to achieve sufficient durability. A structure supported in this manner also enables the formation of a tubular reaction chamber having a rectangular cross-section and having a large chamber in relation to the wall thickness.

BRIEF DESCRIPTION OF THE DRAWINGS

The invention is described below in detail by making reference to the appended drawings that illustrate some of the embodiments of the invention, in which.

DETAILED DESCRIPTION

Figure 1:
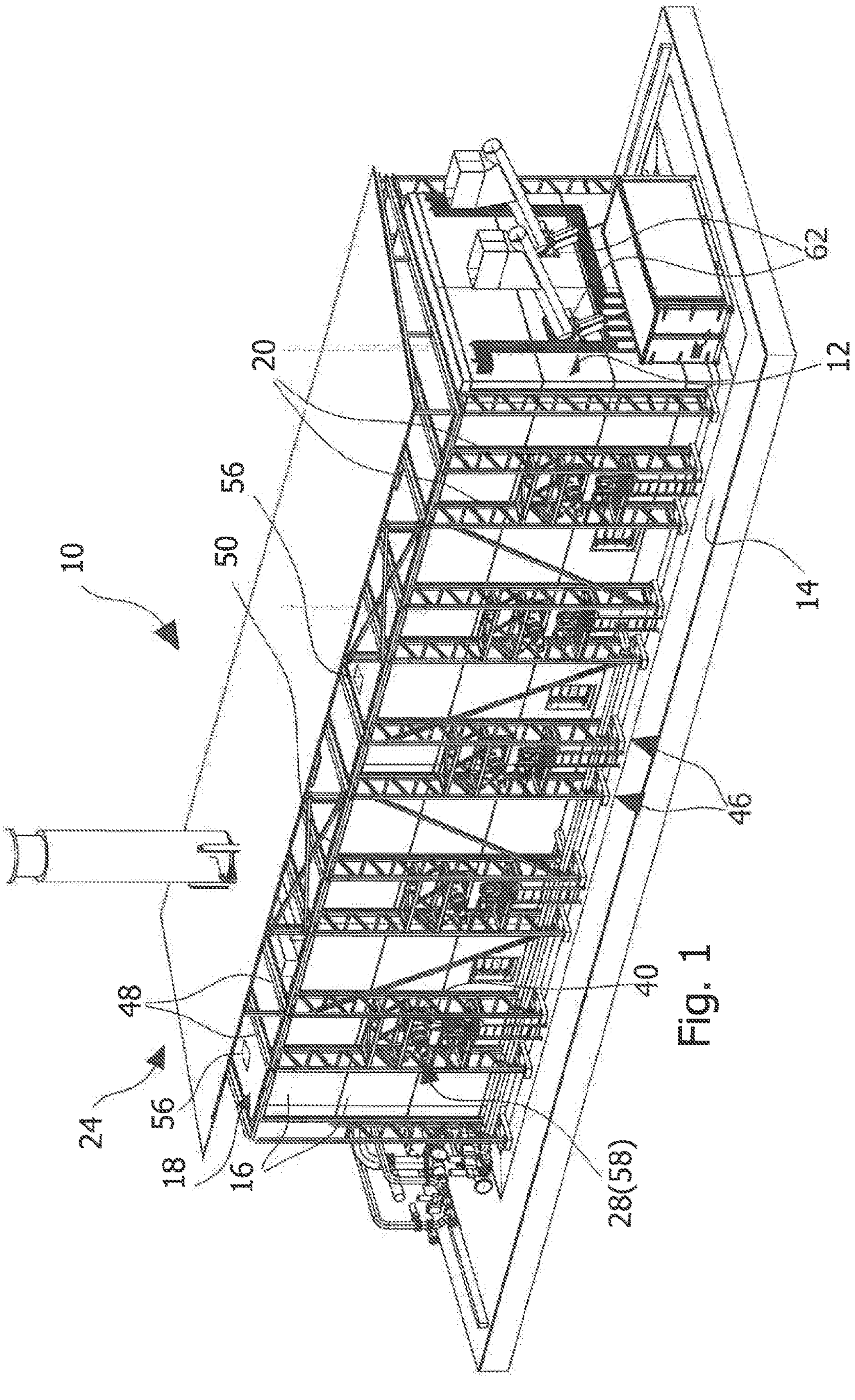
FIG. 1 is an axonometric view of a reactor according to the invention.

A reactor 10 according to the invention comprises in all of its embodiments an external support frame structure 24 of a tubular reaction chamber 12 shown in FIG. 1. The reaction chamber 12 is composed of a bottom 14, walls 16 connected thereto and a ceiling 18 connected to the walls 16. The structure composed of the shell elements 16*a* and 16*b* of the walls 16 is described in more detail below. The terms bottom, walls and ceiling do not limit their placement in a reactor, but they are designated to provide understanding of the structure of the reactor in relation to the direction of travel of the organic raw material in the reactor. The reaction chamber naturally also includes inlet and outlet openings 62, via which raw material is supplied to the reaction chamber 12 advantageously with feed equipment included in the reactor. The external support frame structure 24 is arranged on the outer surface 22 included in the reaction chamber 12 for stiffening the reaction chamber 12. Advantageously, the external support frame structure 24 includes plate stiffeners 20 which are located on the inner surfaces of opposite shell elements for stiffening the shell elements. Advantageously, the external support frame structure 24 also locks the shell elements attaching thereto firmly to each other. The locking of the shell elements 16*a* and 16*b* to the external support frame structure can be implemented by screwing the shell elements 16*a* and 16*b* to the external support frame structure 24 according to FIG. 2. Alternatively, the elements can be fastened to the external support frame structure with separate bondings on the surface of the elements, to which the external support frame structure is bolted. The external support frame structure 24 is arranged to support the reaction chamber 12 during installation and concreting of the shell elements, as well as externally against forces generated by the raw material.

The reactor is meant for producing biogas via anaerobic digestion from organic raw material, such as household or agricultural waste. As a consequence of anaerobic digestion, the water content of raw material increases as digestion progresses and the water content of material in the reaction chamber is high, since the dry content of the material in the reaction chamber can preferably range between 10% and 40% by weight of dry matter. This high water content and the high filling rate of the reaction chamber result in that the material generates hydrostatic pressure that acts on the walls of the reaction chamber and tends to push the walls of the reaction chamber outwards. The filling rate of the reaction chamber is preferably such that the liquid level extends to a distance of 0.5-1.5 m from the ceiling of the reaction chamber. However, on the basis of aforementioned dry matter content, it can be stated that a reactor according to the present embodiment of the invention is a so-called dry digestion reactor. The invention is however not necessarily limited to these.

FIGS. 1-6 illustrate a preferred embodiment of a reactor according to the invention, in which the wall 16 of the reaction chamber 12 is formed by using modular shell elements 16*a* and 16*b* according to the invention. The structure is seen particularly in FIGS. 5 and 6. These illustrate that the wall 16 forming the shell is composed of the outer shell elements 16*a* as well as from the inner shell elements 16*b*. Modular shell elements are preferably 8 cm thick, 240 cm high and up to 1300 cm long components, which are connected to each other for forming at least the walls and preferably also the ceiling of the reaction chamber. In this context, when referring to walls 16, both the side walls and the end walls are meant. The shell elements can be so-called sandwich elements, which have, for example, steel casings and insulation 16*a*' and 16*b*' (see FIGS. 5 and 6) between the casings. Insulation can be, for example, mineral wool or similar. Hence, the outer surface 22 is formed by the surface outside of the outer shell elements 16*a* and facing to the support frame structure 24.

Let it be mentioned that the ceiling 18 of the reaction chamber 10 can be formed as a structure similar to the walls 16 according to the invention, but the structure of the ceiling 18 may also vary from this. The structure of the ceiling (by layers) may be, for example, as follows from the inside outwards: shell element, concreting, insulation, upper surface cast from concrete. In this case, the thickness of the upper surface is thinner than the thickness of the actual concreting, being, for example, approximately 5 cm.

An advantage of a reactor according to the invention when using this type of reaction chamber is that remarkable material savings are achieved, when the walls and the ceiling of the reaction chamber can be manufactured thinner than in prior art solutions and from thinner material thicknesses, because sufficient rigidity is assured by concreting 17*a*. At the same time, the shell elements 16*a* and 16*b* serve as formwork for concreting.

According to FIG. 1, the external support frame structure 24 can be assembled from tubular beams 44, which form various parts in the external support frame structure 24. The external support frame structure 24 advantageously includes vertical columns 46 placed at a distance from each other on both sides of the reaction chamber 12, transverse support structures 48 connecting the vertical columns 46 on both sides of the reaction chamber 12 and longitudinal support structures 50 connecting the vertical columns 46 in the lengthwise direction relative to the reaction chamber 12. For example, tubular beams can be made of steel and have a diameter of 50-150 mm and wall thickness of 2-6 mm. Tubes are advantageously connected to each other with mechanical joints, for example, with bolted joints and nuts. Tubes can also be made of stainless steel or composite.

Figure 2:
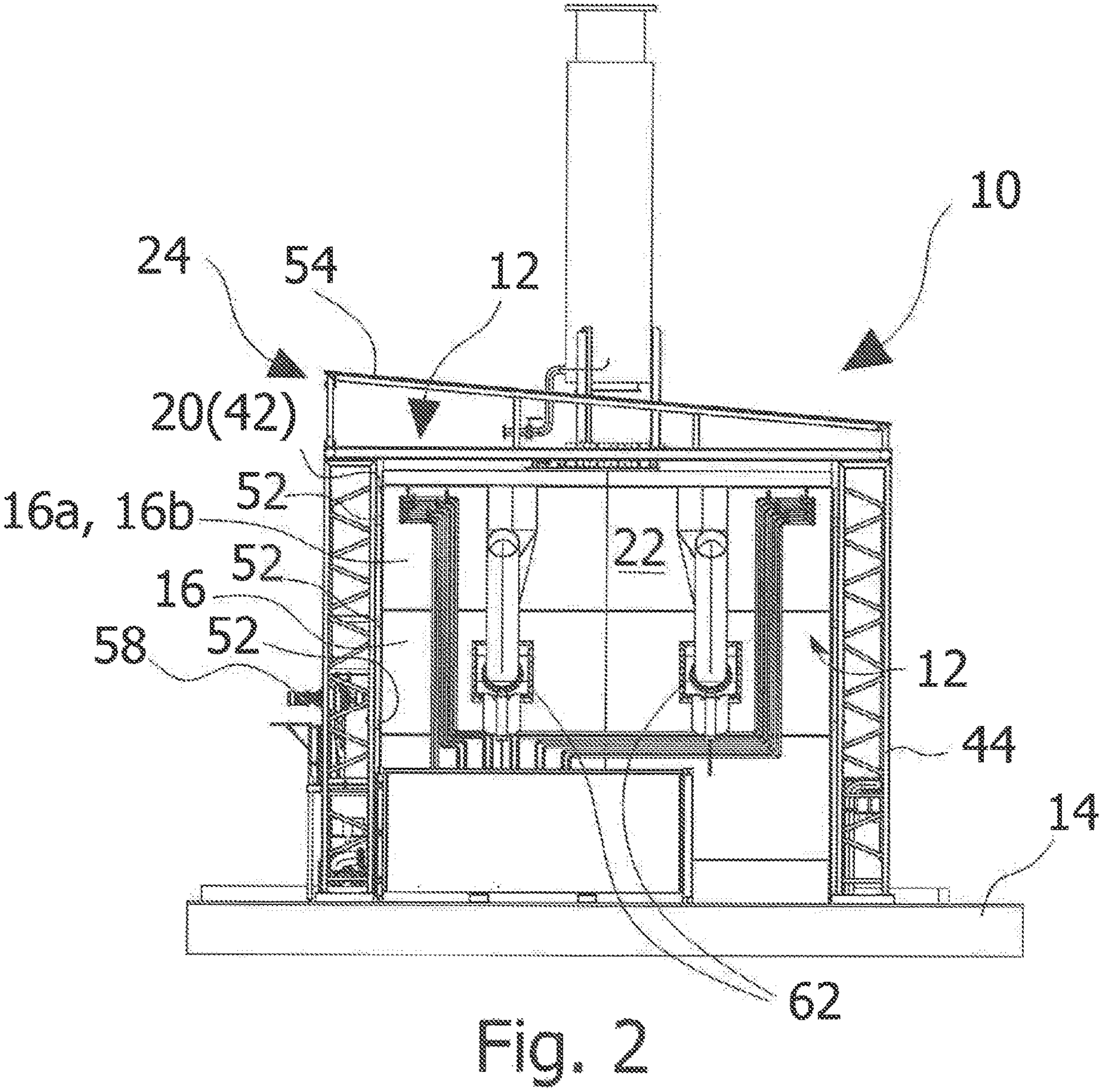
FIG. 2 is an end view of a reactor according to the invention.

FIG. 2 is an end view of a reactor 10 according to the invention. FIG. 2 shows how part of the external support frame structure 24 can be composed of vertical and transverse plate stiffeners 20 which are connected to each other and to the walls 16 of the reaction chamber 12. Advantageously, the plate stiffeners are sheet structures or angle irons 42 which are made of 6-15 mm thick steel or stainless steel. The external support frame structure 24 is advantageously supported by its vertical columns 46 to the outer shell elements 16*a* via spacers 52. According to FIG. 2, the external support frame structure 24 advantageously also includes a ceiling structure 54 forming a pent roof, which can be covered with sheet metal, for example. The external support frame structure 24 is advantageously fixedly fastened to the bottom 14 of the reaction chamber 12, which can be, for example, a concrete slab cast on site. The fastening can be made, for example, using bondings made on the bottom or by bolting the external support frame structure to the bottom.

It can be mentioned separately that the organic raw material in the reactor presented above moves substantially horizontally in the lengthwise direction relative to the reactor. The reactor can also be arranged vertically, whereupon the floor 14 (as well as the ceiling) of the embodiment presented above is a vertical wall (like other walls) and the organic raw material moves vertically or substantially vertically. The term "floor" thus does not limit its placement. In this case, the floor may be structurally similar to the walls 16.

Figure 3:
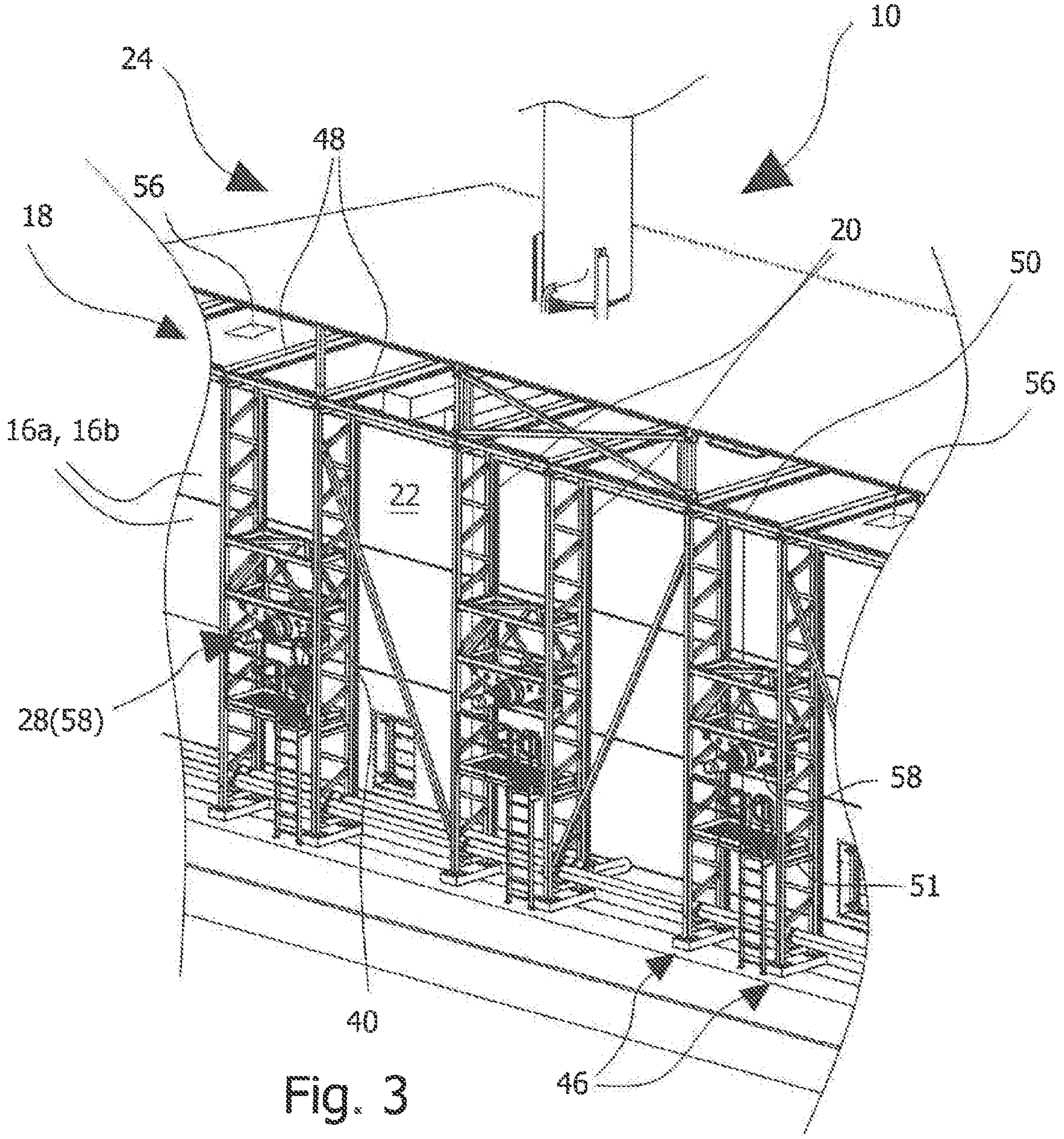
FIG. 3 is an enlargement of FIG. 1.

FIGS. 1-3 show a reaction chamber 12 assembled from the outer and inner shell elements 16*a* and 16*b* of a reactor according to the invention. In this embodiment, three shell elements are stacked one on top of the other on the wall 16 of the reaction chamber 12. When the height of a single shell element is 240 cm, the height of the reaction chamber 12 will be 720 cm. Correspondingly, there are four successive shell elements 16*a* and 16*b* in the reaction chamber 12 wall, whereupon when the length of a single shell element is 8.25 m, the length of the entire reaction chamber 12 will be 33 m. Similar shell elements 16*a* and 16*b* of the same or different length can also be used transversely placed in the ceiling 18 of the reaction chamber 12, whereupon the width of the reaction chamber may be 8.25 m or, for example, 11 m. If required, in the ceiling (and in the end walls) can then be used shell elements having lengths of different dimensions, whereupon the width of the reaction chamber 12 is not defined by the lengths of the shell elements used in the side walls.

Figure 4:
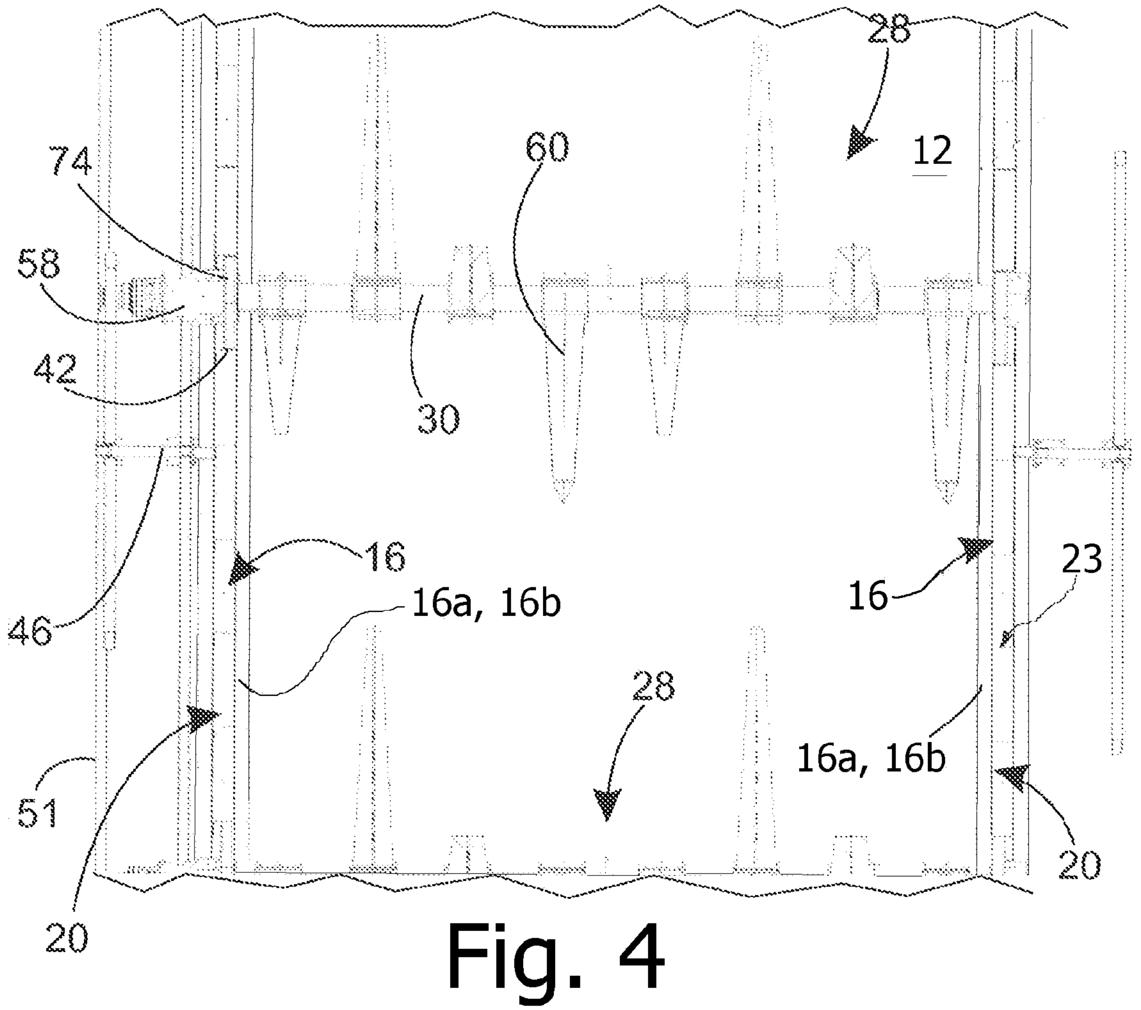
FIG. 4 is a top view of a reactor according to the invention, cut horizontally in the lengthwise direction relative to the frame.
Figure 5:
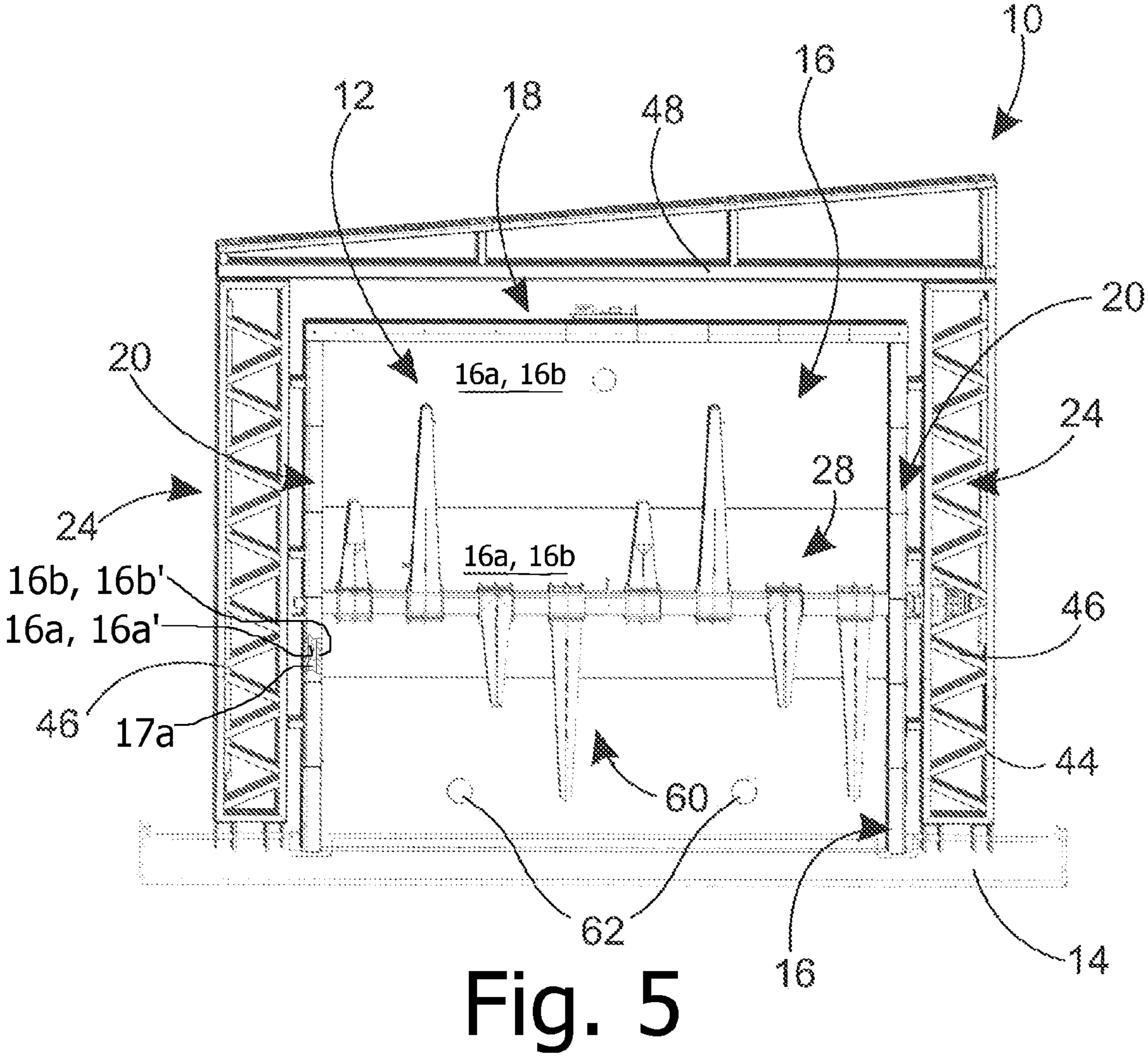
FIG. 5 is an end view of a reactor according to the invention, cut vertically in the transverse direction relative to the frame.

FIGS. 1 and 3 depict, shown with reference numeral 40, the lead-throughs of the agitation and transfer equipment preferably included in the reactor, through which the rotation axis 30 of the agitation and transfer equipment 28 is led according to FIGS. 4 and 5. The ceiling 18 of the reaction chamber 12 may include transparent inspection doors 56, via which it is possible to monitor the filling rate of the reaction chamber and operation of the agitation and transfer equipment.

FIGS. 1 and 3 also depict that the external support frame structure 24 does not cover the entire surface area of the reaction chamber walls, but supports the reaction chamber walls via the plate stiffeners and edged reinforcements on the outer surface of the walls only at selected points. The vertical columns 46 in the external support frame structure 24 are evenly or unevenly distributed at a distance from each other over the length of the reaction chamber; however, additional vertical columns 46 and transverse support structures 48 may also be included at both ends for extending the ceiling constructions slightly over the reaction chamber. Advantageously, at least one side of the external support frame structure includes support irons 51 (FIG. 3) for a maintenance level, on which the maintenance level is formed. In the embodiment of FIGS. 1-6, the vertical columns 46 are advantageously placed at an interval of 3-6 meters. The external support frame structure of the reactor according to the invention can be partly assembled already at the manufacturing site regarding, for example, vertical columns and transverse support structures, or alternatively, it is also easy to assemble the structures at the assembly site, since, due to bolted joints, erection of the external support frame structure does not require welding. Edged reinforcements and plate stiffeners are advantageously welded to the elements already during the manufacture of the elements in the factory.

FIG. 3 shows an enlargement of the reactor of FIG. 1. According to FIG. 3, the drive motors 58 of the agitation and transfer equipment can be supported to the external support frame structure 24, whereupon the shell elements 16*a* and 16*b* of the reaction chamber 12 do not need to carry the load of the agitation and transfer equipment 28, at least not significantly. This, in turn, enables the manufacture of the reaction chamber walls as fairly thin structures. The number of agitation and transfer devices is the same as that of the agitation zones, since the material in the reaction chamber is agitated preferably as needed in each agitation zone.

FIG. 4 is a horizontal cross-sectional view showing how the rotation axis 30 of the agitation and transfer equipment 28 is supported with bearings 74 to the plate stiffeners 20 of the external support frame structure 24. FIG. 4 also shows the blades 60 included in the agitation and transfer equipment 28. According to FIG. 4, the shell elements 16*a* and 16*b* (also depicted in FIG. 5 as a partial section of the structure) forming the walls 16 of the reaction chamber 12 can be quite thin when there are, leaning immediately against these, plate stiffeners 20, which in turn lean against the vertical columns 46 of the external support frame structure 24.

FIG. 5 clearly illustrates how the vertical columns 46 of the external support frame structure support the shell elements 16*a* on the outer surface of the reaction chamber 12 via a spacer 52. The spacer can also be an integral part, for example, a HEA beam, from the footing up to the upper edge of the element. In turn, the external support frame structure 24 can be fastened to bondings cast on the bottom 14.

Figure 6:
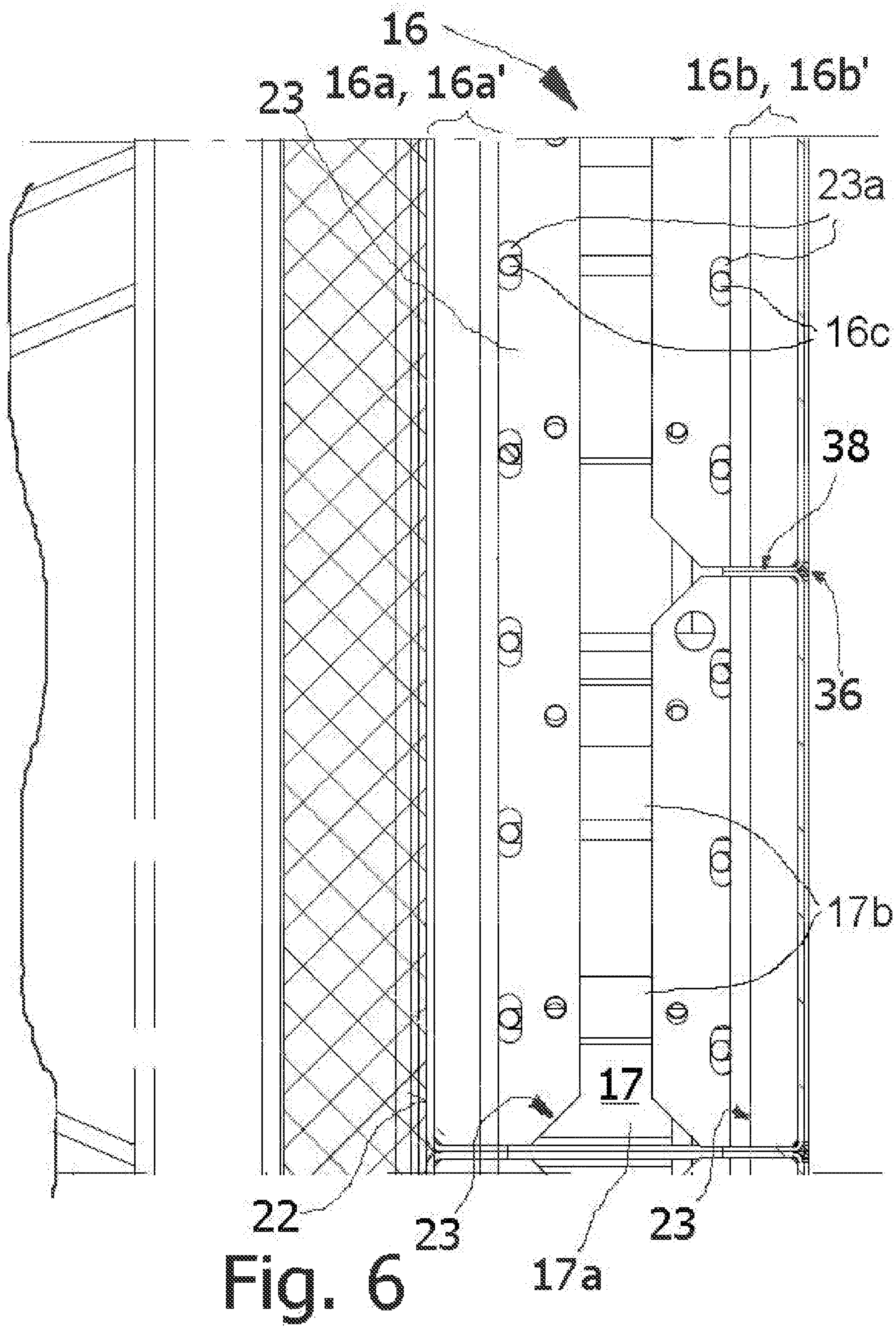
FIG. 6 is a cross-sectional view of the joining of superimposed shell elements of the reaction chamber of a reactor according to the invention.

FIG. 6 shows a partial cross-sectional view of the seals 36 between the shell elements 16*a* and 16*b* stacked on top of each other, preventing the material in the reaction chamber from exiting in particular from the seam 38 between the shell elements 16*a* and 16*b*, in particular the inner shell elements 16*b* and, on the other hand, access of external moisture into the shell elements 16*a* and 16*b*, in particular into the outer shell elements 16*a*, into the insulation 16*b*'. On the inside, the seams can also be sealed with adhesive paste, for example, or by welding. This also shows the shell structure of a reaction chamber according to the invention, in which between the outer and inner shell elements 16*a* and 16*b* remains a filling space or housing 17 which is concreted 17*a*. In addition to this, on the inner surfaces of opposing shell elements 16*a*, 16*b* are plate stiffeners 17*b* for forming a stiffening casing structure. It is also preferred that each shell element 16*a*, 16*b* includes an edged reinforcement 23 arranged to circulate the element 16*a*, 16*b*, as well as on the inner surface of the shell element 16*a*, 16*b* for vertically reinforcing the shell element 16*a*, 16*b*.

Further, in connection with the shell elements are advantageously arranged reinforcing steel bars 16*c*. They are advantageously led through both the edged reinforcements 23 and the plate stiffeners 17*b*. For this purpose, the edged reinforcements 23 are equipped with holes 23*a* and the plate stiffeners 17*b* are equipped with holes (not shown in FIG. 6) in order that the elongated reinforcing steel bars 16*c* can be positioned at the desired site.

With shell part, to which the structure according to the invention is adapted, is meant here at least the side and end walls 16 of the reactor 10, and possibly also the ceiling 18. It is also feasible that, instead of concrete, a structure according to the invention can also be adapted to the floor, when the reactor is arranged into an upright position.

A reactor design according to the invention implemented by using a thin reaction chamber and an external support frame structure can also be applied in other uses, wherein the reactor contains a large amount of material in a high liquid content, which generates a high hydrostatic pressure in a high reaction chamber.

The invention claimed is:

1. A reactor for manufacturing biogas from organic raw material using anaerobic digestion, the reactor including a tubular reaction chamber composed of a bottom, walls and a ceiling for processing the raw material into end products, and agitation and transfer equipment arranged in the reaction chamber, wherein the reactor further includes an external support frame structure arranged on an outer surface of the reaction chamber for stiffening and supporting the reaction chamber externally against the forces generated by the raw material, wherein a shell of the reaction chamber of the reactor is composed of outer shell elements and inner shell elements placed at a distance from each other inside a space defined by the external support frame structure, which together form a housing structure of the shell, wherein a filling space or housing between the outer shell elements and the inner shell elements is filled with concrete, wherein each of said outer shell elements and of said inner shell elements is a sandwich element having steel casings and insulation between the steel casings, and wherein inside the filling space or housing on inner surfaces of opposing outer shell elements and inner shell elements of the shell are plate stiffeners which form a stiffening casing structure.

2. The reactor according to claim 1, wherein said agitation and transfer equipment is supported to said external support frame structure.

3. The reactor according to claim 1, wherein the height of the reactor is 6-15 m.

4. The reactor according to claim 3, wherein the height of the reactor is 8-10 m.

5. The reactor according to claim 1, wherein the outer shell elements and the inner shell elements on the walls of the reaction chamber have a height ranging 0.5-3.6 m.

6. The reactor according to claim 5, wherein the outer shell elements and the inner shell elements on the walls of the reaction chamber are modularly dimensioned in height.

7. The reactor according to claim 5, wherein the outer shell elements and the inner shell elements on the walls of the reaction chamber have a height ranging 0.5-2.4 m.

8. The reactor according to claim 1, wherein the outer shell elements and the inner shell elements on the walls of the reaction chamber have a length of 6 13 m.

9. The reactor according to claim 8, wherein the outer shell elements and the inner shell elements on the walls of the reaction chamber have a length of 10-11 m.

10. The reactor according to claim 8, wherein the outer shell elements and the inner shell elements on the walls of the reaction chamber are modularly dimensioned in length.

11. The reactor according to claim 1, wherein corners of the reactor have a separate angle joint piece, whereupon at least the outer shell elements and the inner shell elements in the lengthwise direction relative to the wall are standard structures.

12. The reactor according to claim 1, wherein the plate stiffeners have holes for reinforcement steel bars.

13. The reactor according to claim 12, wherein each outer shell element and inner shell element includes an edged reinforcement arranged to circulate the outer shell element and inner shell element as well as on the inner surface of the outer shell element and inner shell element for vertically reinforcing the outer shell element and inner shell element, the edged reinforcement having holes for the reinforcement steel bars.

14. The reactor according to claim 1, wherein the external support frame structure includes the plate stiffeners fastened to the outer surface of the reaction chamber.

15. The reactor according to claim 1, wherein the thickness of the walls of the reaction chamber is 200-500 mm.

16. The reactor according to claim 15, wherein the thickness of the walls of the reaction chamber is 250-350 mm.

17. The reactor according to claim 1, wherein said reaction chamber includes sealed lead-throughs for the agitation and transfer equipment for keeping liquid raw material or end products in the reaction chamber.

18. The reactor according to claim 1, wherein said external support frame structure is composed of tubular beams welded to each other.

19. The reactor according to claim 18, wherein said external support frame structure includes:

vertical columns arranged at a distance from each other in the lengthwise direction relative to the reactor on both sides of the reactor, transverse support structures for connecting the vertical columns in the transverse direction relative to the reactor, and longitudinal support structures for connecting the vertical columns to each other in the lengthwise direction relative to the reactor on each side of the reactor.

* * * * *